United States Patent [19]
Mui et al.

[11] Patent Number: 5,393,910
[45] Date of Patent: Feb. 28, 1995

[54] PROCESS FOR MAKING ISOCYANATOORGANOSILANES

[75] Inventors: Jeffrey Y. P. Mui, Bellingham, Mass.; Mark P. Bowman, Marietta, Ohio

[73] Assignee: OSi Specialties, Inc., Danbury, Conn.

[21] Appl. No.: 138,225

[22] Filed: Oct. 20, 1993

[51] Int. Cl.$^6$ .............................................. C07F 7/10
[52] U.S. Cl. .................................................. 556/414
[58] Field of Search ........................................ 556/414

[56] References Cited

U.S. PATENT DOCUMENTS

| | | |
|---|---|---|
| 3,170,891 | 2/1965 | Speir . |
| 3,494,951 | 2/1970 | Berger . |
| 3,511,866 | 5/1970 | Pepe . |
| 3,517,001 | 6/1970 | Berger . |
| 3,584,024 | 6/1971 | Pepe . |
| 3,598,852 | 8/1971 | Berger . |
| 3,607,901 | 9/1971 | Berger . |
| 3,642,854 | 2/1972 | Kozjukov et al. .................. 556/414 |
| 3,821,218 | 6/1974 | Berger . |
| 4,031,120 | 6/1977 | Gervase ............................ 556/414 |
| 4,064,151 | 12/1977 | Hedaya et al. . |
| 4,113,691 | 9/1978 | Ward . |
| 4,146,585 | 3/1979 | Ward et al. . |
| 4,330,479 | 5/1982 | Merger et al. . |
| 4,654,428 | 3/1987 | Kurashima et al. . |
| 4,736,046 | 4/1988 | Chang . |
| 4,870,198 | 9/1989 | Mormann et al. .................. 556/414 |
| 5,218,133 | 6/1993 | Pepe et al. . |

OTHER PUBLICATIONS

Mironov, et al., "Synthesis of Carbofunctional Organosilicon Compounds Containing Isocyanate, Chlorocarbonate, and Carbamate Groups by Hydrosilylation", *Proc. Natl. Acad. Sci. USSR*, 178(2):37–40 (1968).

*Kirk–Othmer Encyclopedia of Chemical Technology*, Wiley & Sons, vol. 4, p. 763 (1978).

Chikina, et al., "Thermal Rearrangement of Siloxyphenylene Isocyanates", *Chemical Abstracts*, 100:209960r (1984); translated from Ahurnal Obshchei Khimii, vol. 54, No. 1, pp. 139–145 (1984).

Saunders, et al., "Polyurethanes Chemistry and Technology", *High Polymers*, vol. XVI, part I, pp. 314–317 (1962).

Ashby, "New 3-Isocyanatopropylsilanes", *J. Chem. Eng. Data*, 18(2):238–239 (1973).

Boecker, et al., "Method and Apparatus for Manufacturing Highly Pure Silicon Carbide Powder", *Chemical Abstracts* 91:111614b (1979).

*Primary Examiner*—Paul F. Shaver
*Attorney, Agent, or Firm*—Banner, Birch, McKie & Beckett

[57] ABSTRACT

A method is described for the preparation of an isocyanatoorganosilane by an elevated temperature thermally induced decomposition of a carbamatoorganosilane in the gas phase preferably under ambient or reduced pressure.

9 Claims, No Drawings

PROCESS FOR MAKING ISOCYANATOORGANOSILANES

FIELD OF THE INVENTION

The present invention relates to a method of preparing isocyanatoorganosilanes and to certain isocyanatoorganosilanes so prepared.

BACKGROUND OF THE INVENTION

There has been a continuing need for a method of preparing isocyanatoorganosilanes, including isocyanatoalkylsilanes, in high yields and purities from economical and relatively non-hazardous raw materials without generating significant quantities of hazardous by-products and waste materials. Heretofore, isocyanatoorganosilanes have been made in relatively low volumes by inefficient or costly processes.

For example, isocyanatoorganosilanes have been prepared by processes involving addition of hydrosilanes to unsaturated isocyanates, particularly allyl isocyanate, in the presence of a noble metal catalyst. Allyl isocyanate is a highly toxic raw material of limited commercial availability.

Processes are also known in the art wherein isocyanatoalkylsilanes are prepared from carbamatoalkylsilanes at a low temperature in the liquid phase, or from aminoalkylsilanes and highly toxic phosgene by various routes. All liquid phase processes disclosed thus far suffer from one or more disadvantages of low yield, slow kinetics, need for highly toxic raw materials, need for extensive work-up or purification often in the presence of higher levels of close-boiling contaminants, and substantial generation of by-products and waste materials.

A method for making 2-isocyanatoethoxysilanes by liquid phase thermal rearrangement of N-silyl-2-oxazolidinones has also been disclosed. The bonding of the isocyanatoalkyl group to silicon atoms in these molecules is through a hydrolyzable silicon-oxygen bond, and the silane moiety does not contain additional alkoxy groups as are present and often necessary in current commercially useful isocyanatoalkylsilanes.

The present invention surprisingly provides a method wherein isocyanatoorganosilanes are provided in high yields and purities with no need to use highly toxic phosgene or highly toxic allyl isocyanate, with no generation of highly corrosive hydrogen chloride as a by-product, with no need to use inert solvents as diluents, and with minimal formation of by-products, contaminants, and waste materials. Because the method of the present invention can be operated continuously with very short residence times, a relatively small reactor is capable of large throughputs with a correspondingly small capital investment.

The method of the present invention can also provide isocyanatoorganosilanes which have not been prepared by methods known to those skilled in the art, including isocyanatoorganosilanes in which the isocyanate groups are attached to silicon atoms through branched hydrocarbon groups. Such branched hydrocarbon groups respond to a need for isocyanatoorganosilanes having isocyanate groups with varying degrees of reactivity, which provide corresponding desirable variations in the performance properties of products incorporating said isocyanatoorganosilanes, including wet strength, flexibility, and oxidation resistance.

The method of the present invention can also provide isocyanatoorganosilanes wherein the silicon atom bearing the isocyanatoorgano group is further substituted by siloxy groups. These compounds combine the high surface activity of low molecular weight siloxanes with the high reactivity of the isocyanate group, and are useful in providing improved coatings, particularly for metallic substrates such as in automotive applications.

SUMMARY OF THE INVENTION

The present invention provides a method of preparing isocyanatoorganosilanes. The method simply involves vaporizing a carbamatoorganosilane and heating said vaporized carbamatoorganosilane in a reaction zone at an elevated temperature for a time sufficient to form said isocyanatoorganosilane. Specific isocyanatoorganosilanes that can be prepared include those having the general formula $R_x(R''O)_{3-x}SiR'NCO$ wherein x is an integer having a value of 0, 1, 2, or 3, each R separately represents an alkyl group or halogenated alkyl group of 1 to 12 carbon atoms, a cycloalkyl group or halogenated cycloalkyl group of 5 to 8 carbon atoms, an aryl group of 6 to 14 carbon atoms, or an alkaryl or aralkyl group of 7 to 15 carbon atoms, each R'' separately represents R or a silyl group $R_3Si—$, or a siloxy group $R_3Si(OSiR_2)_m—$ wherein m is an integer having a value of 1 to 4, or when x is 0 or 1 two R'' groups together may form a divalent siloxy group $—R_2(OSiR_2)_n—$ wherein n is an integer having a value of 3, 4, or 5 thus forming a cyclic siloxane with the silicon atom bearing the isocyanatoorgano group, and R is as defined above, R' represents a divalent hydrocarbon group of 1 to 20 carbon atoms, preferably a linear or branched divalent saturated or unsaturated hydrocarbon group of 1 to 20 carbon atoms attached to silicon by a silicon-carbon bond, including linear and branched alkylene, arylene, alkarylene, and aralkylene groups, and wherein R and R' may also contain heteroatom functional groups such as ether, thioether, sulfone, ketone, ester, amide, nitrile, or halogen.

The method involves the elevated temperature thermally induced decomposition in the gas phase generally at ambient or reduced pressure of a carbamatoorganosilane of the general formula $R_x(R''O)_{3-x}SiR'NHCO_2R$ wherein R, R'', R', and x are as defined above. While the R and R'' groups may vary within the product isocyanatoorganosilane or starting carbamatoorganosilane molecules, the R and R'' groups attached to the oxygen atoms in the isocyanatoalkylsilanes will generally, but not necessarily, be the same.

Thus, the method of the present invention is represented by the following general equation:

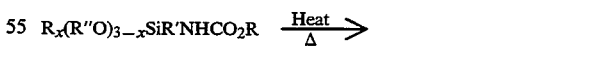

$$R_x(R''O)_{3-x}SiRNCO + ROH$$

wherein R, R'', R' and x are as defined above. Preferably the reaction is conducted at an elevated temperature of 300° to 600° C. The method of the present invention can be performed in continuous fashion in any flow-through apparatus having the capacity for maintaining an inert diluent atmosphere or a reduced pressure, for vaporizing the carbamatoorganosilane raw materials, for providing a heated reaction zone at an elevated temperature, preferably in the range of about 300°–600° C., for removing the ROH by-product, for maintaining physical integrity against the relatively high reaction temperatures, and for minimizing thermal conversion of the isocyanato-organosilanes so formed to silicon-containing ceramic compositions which can accumulate in the apparatus.

While organic hydrocarbon isocyanates have been prepared at high temperatures in flow-through equipment, the use of such a method to convert carbamatoorganosilanes cleanly and at high yield to isocyanatoorganosilanes was unexpected in view of the high temperature thermal conversions of a variety of organosilicon compounds to silicon-containing ceramic compositions, namely silicon carbide, silicon nitride, silicon oxycarbide, and mixtures thereof that one would have expected to occur.

While not wishing to be bound by theory, it may be that the gas phase preparation of isocyanatoorganosilanes can occur at a higher yield than in the prior liquid phase preparation because the gas phase process, in essence, may permit the reaction to proceed more on a unimolecular scale. Vaporization of carbamatoorganosilanes in principle separates each silane molecule from closely bound equivalent molecules as encountered in the liquid phase. Thus, by-product or heavies formation by bimolecular or trimolecular reactions which occur in the liquid phase may be reduced or avoided in the gas phase. Furthermore, applicant has found that the avoidance of any build-up of non-volatile residue in the reactor can be aided by adjusting the rate that the vaporized carbamatoorganosilane is introduced into the reaction zone. The most appropriate rate for a particular reactor depends on a variety of factors, but can readily be determined by one skilled in the art using routine optimization.

One side reaction encountered in the liquid phase but not in the gas phase is the formation of close-boiling cyclic silyl carbamates from isocyanatoorganosilanes, with which they are isomeric. Simply heating isocyanatoorganosilanes, where R'' is a methyl or ethyl group, in the liquid phase to about 140° C. causes

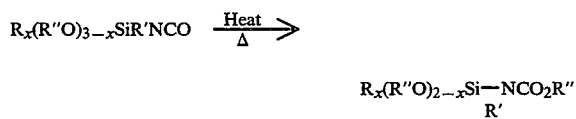

significant rearrangement of isocyanatoorganosilane to cyclic silyl carbamate where x is 0, 1, or 2. Correspondingly, isocyanatoorganosilanes prepared in the liquid phase contain significantly higher contents of cyclic silyl carbamates as close-boiling contaminants, compared to the same materials prepared by the present invention.

Under optimal conditions, the method of the present invention provides isocyanatoorganosilane products requiring no further purification for industrial use. Where an impurity is present, the impurity is essentially the starting carbamatoorganosilane, which can be removed by simple distillation and recycled to provide additional product.

The products of the method of the present invention, namely isocyanatoorganosilanes, and particularly $(MeO)_3Si(CH_2)_3NCO$ and $(EtO)_3Si(CH_2)_3NCO$, are articles of commerce, with numerous uses in manufacturing industries. One use, for example, is in the preparation of silane-grafted polymers as disclosed in U.S. Pat. Nos. 4,113,691 and 4,146,585.

DETAILED DESCRIPTION OF THE INVENTION

The present invention provides a method of preparing an isocyanatoorganosilane by elevated temperature thermally induced decomposition of a carbamatoorganosilane preferably at a temperature in the range of about 300° to 600° C. in the gas phase generally under ambient or reduced pressure. Preferably the method is used to prepare an isocyanatoorganosilane having the general formula $R_x(R''O)_{3-x}SiR'NCO$ from a carbamatoorganosilane having the general formula $R_x(R''O)_{3-x}SiR'NHCO_2R$ according to the equation:

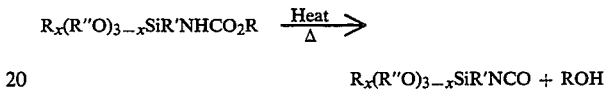

wherein x is an integer having a value of 0, 1, 2, or 3, each R separately represents an alkyl group or halogenated alkyl group of 1 to 12 carbon atoms, a cycloalkyl group or halogenated cycloalkyl group of 5 to 8 carbon atoms, an aryl group of 6 to 14 carbon atoms, or an alkaryl or aralkyl group of 7 to 15 carbon atoms, each R'' separately represents R or a silyl group $R_3Si-$, or a siloxy group $R_3Si(OSiR_2)_m-$ wherein m is an integer having a value of 1 to 4, or when x is 0 or 1 two R'' groups together may form a divalent siloxy group $-SiR_2(OSiR_2)_n-$ wherein n is an integer having a value of 3, 4, or 5, thus forming a cyclic siloxane with the silicon atom bearing the isocyanatoorgano group, and R is as defined above, R' represents a linear or branched divalent saturated or unsaturated hydrocarbon group of 1 to 20 carbon atoms attached to silicon by a silicon-carbon bond, including alkylene, arylene, alkarylene, and aralkylene groups, and wherein R and R' may also contain heteroatom functional groups such as ether, thioether, sulfone, ketone, ester, amide, nitrile, or halogen. It should be recognized that the R, R', R'', and heteroatom functional groups in the starting materials and products are those which can be subjected to the conditions of the method without adverse chemical change. While the R and R'' groups may vary within the isocyanato-organosilane and carbamatoorganosilane molecules, the R and R'' groups attached to oxygen atoms in said isocyanatoorganosilanes will generally, but not necessarily, be the same.

The method of the present invention generally is performed in continuous fashion in any flow-through apparatus having the capability for maintaining an inert atmosphere, for vaporizing the carbamatoorganosilane raw material, for maintaining a heated reaction zone at an elevated temperature preferably in the range of about 300° to 600° C., for removing the ROH by-product, for maintaining physical integrity against the relatively high reaction temperature, and for minimizing thermal conversion of the isocyanatoorganosilane products so formed to silicon-containing ceramic compositions. The apparatus may be constructed from metal, alloy, glass, or ceramic material, and may be connected to ancillary equipment as needed for feeding the carbamatoorganosilane to the vaporizer/heated reaction zone, and for collecting and optionally purifying the isocyanatoorganosilane products. Reaction conditions are not narrowly critical, since yields can be optimized by adjusting residence times and temperatures in a given apparatus. The method of the present invention can also be operated at atmospheric, subatmospheric, or superatmospheric pressures. However, atmospheric or subatmospheric pressures in the range of 10 mm–760 mm are normally preferred. Various catalysts are known in the art for catalyzing the decomposition of carbamates to isocyanates and alcohols. However, the use of a catalyst in the method of the present invention is optional.

Thermal input to the carbamatoorganosilane vaporizer and heated reaction zone can be provided by superheated steam, flame furnace, or by electrical heaters, and controlled and measured by standard devices for that purpose. Configuration of such total equipment regarding direction of flow, multiplicity and size of contained flows, and shape or pattern of flow are also not narrowly critical. One assembly of equipment, generally referred to as a hot tube reactor, is well known in the art and is in use in the commercial production of various chemicals which require high temperature process steps in the gas phase.

A preferred apparatus for conducting the process of the present invention on a laboratory scale comprises a stainless steel tube packed with stainless steel saddles. Thermal input is provided electrically. The system can be operated at 300 to 760 mm pressure, with vaporizer temperatures in the 340° to 380° range, and heated reaction zone temperatures in the 400° to 520° range.

It is understood that various mechanical devices known in the art, such as spray nozzles or atomizers, may be used to assist in vaporizing the carbamatoorganosilane raw materials, and that the vaporizer temperature need not be different from that of the temperature prevailing in the reaction zone.

Preferred carbamatoorganosilanes and the resulting isocyanatoorganosilane products are those wherein the R groups have 1 to 4 carbon atoms, and most preferably 1 to 2 carbon atoms. Alkyl groups are preferred, i.e., methyl or ethyl groups. Preferred R" groups are R groups, trimethylsilyl groups, or divalent siloxy groups, —SiMe$_2$(OSiMe$_2$)$_n$—, where n is 3 or 4, formed from two R" groups when x is 1. Preferred R' groups are linear or branched divalent hydrocarbon groups containing 1 to 11 carbon atoms of the formula —C$_n$H$_{2n}$—, preferably where n is an integer of 3 to 6, and most preferably the divalent hydrocarbon group —(CH$_2$)$_3$—. It is understood that the divalent hydrocarbon group —C$_n$H$_{2n}$— can be branched, and that the isocyanate group of the product may be attached to a primary, secondary, or tertiary carbon atom. Thus, isocyanatoorganosilanes, R$_x$(R"O)$_{3-x}$SiR'NCO, wherein R' is selected from the group of —CH$_2$CH$_2$CMe$_2$—, —CH$_2$CH$_2$CHMeCH$_2$—, —CH$_2$CH$_2$CMe$_2$CH$_2$—, and —CH$_2$CHMeCH$_2$— where Me is a methyl group, are also preferred embodiments of the present invention. Preferred values of x include 0, 1, and 2, with the values of 0 and 1 being most preferred.

Carbamatoorganosilanes useful in the method of the present invention for making isocyanatoorganosilanes may be selected from the group of:

(MeO)$_3$Si(CH$_2$)$_3$NHCO$_2$Me, Me(MeO)$_2$Si(CH$_2$)$_3$NHCO$_2$Me, Me$_2$(MeO)Si(CH$_2$)$_3$NHCO$_2$Me, (EtO)$_3$Si(CH$_2$)$_3$NHCO$_2$Et, Me(EtO)$_2$Si(CH$_2$)$_3$NHCO$_2$Et, Me$_2$(EtO)Si(CH$_2$)$_3$NHCO$_2$Et, (PrO)$_3$Si(CH$_2$)$_3$NHCO$_2$Pr, (MeO)$_3$SiCH$_2$CHMeCH$_2$NHCO$_2$Me, Me(MeO)$_2$SiCH$_2$CHMeCH$_2$NHCO$_2$Me, (EtO)$_3$SiCH$_2$CHMeCH$_2$NHCO$_2$Et, Me$_2$(MeO)SiCH$_2$CHMeCH$_2$NHCO$_2$Me, Me(EtO)$_2$SiCH$_2$CHMeCH$_2$NHCO$_2$Et, Me$_2$(EtO)SiCH$_2$CHMeCH$_2$NHCO$_2$Et, (MeO)$_3$Si(CH$_2$)$_4$NHCO$_2$Me, Me(MeO)$_2$Si(CH$_2$)$_4$NHCO$_2$Me, Me$_2$(MeO)Si(CH$_2$)$_4$NHCO$_2$Me, Me(EtO)$_2$Si(CH$_2$)$_4$NHCO$_2$Et, (F$_3$CCH$_2$O)$_3$Si(CH$_2$)$_3$NHCO$_2$Me, Me(F$_3$CCH$_2$O)$_2$Si(CH$_2$)$_3$NHCO$_2$Me, Me(EtO)$_2$Si(CH$_2$)$_2$CHMeCH$_2$NHCO$_2$Et, (MeO)$_3$Si(CH$_2$)$_2$CHMeCH$_2$NHCO$_2$Me, Me(MeO)$_2$SiCH$_2$NHCO$_2$Me and the like wherein Me is a methyl group, Et is an ethyl group, and Pr is a propyl group.

The carbamatoorganosilane raw materials may be prepared by any of the variety of methods known in the art, including by reaction of aminoorganosilanes with chloroformate esters, by reaction of hydrosilanes with unsaturated carbamate esters, by reaction of chloroorganosilanes with cyanate salts in the presence of an alcohol, or by reaction of aminoorganosilanes with dialkyl carbonates in the presence or absence of a catalyst. The latter method is the preferred method, and is disclosed in U.S. Pat. No. 5,218,133, assigned to the same assignee as the present invention and incorporated herein by reference. It is understood that virtually any aminoorganosilane can be converted to the corresponding carbamatoorganosilane, and said corresponding carbamatoorganosilane can be converted to the corresponding isocyanatoorganosilane by the method of the present invention, with the provisos that the corresponding carbamatoorganosilane be vaporizable and the corresponding isocyanatoorganosilane be stable under the gas phase reaction conditions.

In addition to those aminoorganosilanes used to prepare the specific carbamatoorganosilane structures shown above, aminoorganosilanes leading to carbamatoorganosilanes useful in the method of the present invention also may be selected from the group of:

(MeO)$_3$Si(CH$_2$)$_2$CMe$_2$NH$_2$, Me(MeO)$_2$Si(CH$_2$)$_2$CMe$_2$NH$_2$, (MeO)$_3$Si(CH$_2$)$_2$CMe$_2$CH$_2$NH$_2$, (EtO)$_3$Si(CH$_2$)$_2$CMe$_2$CH$_2$NH$_2$, Me(MeO)$_2$Si(CH$_2$)$_2$CMe$_2$CH$_2$NH$_2$, Me$_2$(EtO)Si(CH$_2$)$_2$CMe$_2$CH$_2$NH$_2$, (MeO)$_3$SiCH=CHCMe$_2$NH$_2$, Me(MeO)$_2$SiCH=CHCMe$_2$NH$_2$, (MeO)$_3$Si(CH$_2$)$_2$C$_6$H$_4$CH$_2$NH$_2$, Me(EtO)$_2$Si(CH$_2$)$_2$C$_6$H$_4$CH$_2$NH$_2$, (EtO)$_3$Si(CH$_2$)$_3$OC$_6$H$_4$NH$_2$, Me(MeO)$_2$Si(CH$_2$)$_3$OC$_6$H$_4$NH$_2$, (MeO)$_3$Si(CH$_2$)$_3$NHC$_6$H$_4$NH$_2$, Me(EtO)$_2$Si(CH$_2$)$_3$NHC$_6$H$_4$NH$_2$, Me(Me$_3$SiO)$_2$Si(CH$_2$)$_3$NH$_2$, (Me$_3$SiO)$_3$Si(CH$_2$)$_3$NH$_2$, (OSiMe$_2$)$_3$OSiMe(CH$_2$)$_3$NH$_2$, (OSiMe$_2$)$_4$OSiMe(CH$_2$)$_3$NH$_2$, (MeO)$_3$Si(CH$_2$)$_{11}$NH$_2$, (MeO)$_3$SiC$_6$H$_4$NH$_2$, and the like wherein Me and Et are as defined above and C$_6$H$_4$ is a phenylene group.

Isocyanatoorganosilanes having the formula R$_x$(R"O)$_{3-x}$SiR'NCO, wherein R' is a divalent branched hydro-carbon radical of 3 to 11 carbon atoms, preferably one selected from the group of —CH$_2$CH$_2$CMe$_2$—, —CH$_2$CH$_2$CHMeCH$_2$—, —CH$_2$CH$_2$CMe$_2$CH$_2$—, and —CH$_2$CHMeCH$_2$—, and R, R", and x are as defined as above, have not been prepared prior to the present invention. The facile preparation of these molecules by the process of the present invention was unexpected in view of the tendency of branching in the group R' to promote cyclization reactions. For example, the facile cyclization of (MeO)$_3$SiCH$_2$CH$_2$CMe$_2$CH$_2$NH$_2$ is disclosed in copending application Ser. No. 07/993,304, assigned to the same assignee of the present invention.

The isocyanatoorganosilanes, $R_x(R''O)_{3-x}Si(CH_2)_3$-NCO, wherein $R''$ represents a silyl group $R_3Si-$ or wherein two $R''$ groups together form a divalent siloxy group $-SiR_2(OSiR_2)_n-$, and wherein R, n, and x are as defined above, possibly can be prepared by prior art methods, but, with the exception of $(Me_3SiO)_3Si(CH_2)_3$-NCO, have not been so prepared.

Whereas the exact scope of the present invention is set forth in the appended claims, the following specific examples illustrate certain aspects of the present invention and, more particularly, point out methods of evaluating same. However, the examples are set forth for illustrative purposes only and are not to be construed as limitations on the present invention. The abbreviations g, mol, min, sec, cm, mm, and ca respectively represent gram, molecular equivalent, minute, second, centimeter, millimeter, and about; temperature is reported in degrees Centigrade. Yield and by-product percentages are reported as weight-percent values, corrected by appropriate response factors, as determined by gas chromatography. All reactions were run under an inert atmosphere of nitrogen, or under a reduced pressure.

EXAMPLE 1

Preparation of 3-isocyanatopropyltrimethoxysilane

Methyl N-(3-trimethoxysilylpropyl)carbamate (1135 g, 4.79 mols) was fed to a vertically mounted stainless steel hot tube reactor, packed with stainless steel saddles and having a volume of 65 cm$^3$, at a rate of 1.2 g/min. The top of the reactor served as a vaporizer and was maintained at 380° C. while the remainder of the reactor was maintained at 520° C. The reactor pressure was maintained at 400 mm Hg. Product was collected in an air-cooled flask connected to the lower end of the reactor at ambient temperature. Subambient cooling was achieved by the removal of methanol from the crude product by the periodic application of vacuum (ca 5 mm Hg). Removing methanol by the intermittent application of a higher vacuum to the air-cooled flask in which product was collected also inhibited any recombination between the isocyanatoorganosilane and the by-product alcohol that might otherwise have occurred. A total of 988 g (4.82 mols, 93% yield) of 3-isocyanatopropyltrimethoxysilane was collected at a purity of 92%, based on gas chromatographic analysis.

EXAMPLE 2

Preparation of 3-isocyanatopropyltriethoxysilane

Ethyl N-(3-triethoxysilylpropyl)carbamate (52 g, 0.18 mol) was fed to an unpacked stainless steel upflow hot tube reactor having a volume of 66 cm$^3$ (1.05 cm×76 cm) at a rate of 2.6 g/min. The vaporizer was maintained at 340° C. and the remainder of the hot tube at 460° C. The reactor pressure was maintained at ambient atmospheric pressure. Crude product (49.7 g) was collected, containing 39.1 g (0.16 mol, 89% yield) of 3-isocyanatopropyltriethoxysilane, based on gas chromatographic analysis.

EXAMPLE 3

Preparation of 3-isocyanatopropylmethyldimethoxysilane

The procedure of Example 1 was followed using the same reactor, temperatures, and pressure. Methyl N-(3-methyldimethoxysilylpropyl)carbamate (15.4 g, 0.07 mol) was fed to the top of the reactor at a rate of 1.0 g/min. 3-Isocyanatopropylmethyldimethoxysilane (11.6 g, 0.06 mol, 76% yield) was collected at a purity of 86% as determined by gas chromatographic analysis.

EXAMPLE 4

Stability Test of 3-Isocyanatopropyltriethoxysilane

A sample of purified 3-isocyanatopropyltriethoxysilane was passed through the hot tube reactor of Example 2, except that the reactor temperature was 465° C. and the pressure was 300 mm Hg. The residence time in the reactor was 3.0 sec. Only 2.5% of close-boiling by-products were formed, with no formation of uneluted heavies by gas chromatographic analysis. This example shows that products of the process of the present invention are stable in the hot tube reactor under reaction conditions, and that uneluted heavies are not formed from said products under reaction conditions.

EXAMPLE 5

Preparation of 3,3-dimethyl-4-isocyanatobutylmethyldimethoxysilane

Methyl N-(2,2-dimethyl-4-methyldimethoxysilylbutyl)carbamate, $Me(MeO)_2SiCH_2CH_2CMe_2CH_2NH$-$CO_2Me$ (18.4 g), was passed through the apparatus of Example 1 at a rate of 1.4 g/min at 400 mm Hg with the vaporizer at 350° C. and the hot tube at 590° C. The product was stripped under vacuum to yield 15.6 g of $Me(MeO)_2SiCH_2CH_2CMe_2CH_2NCO$ (85% purity by gas chromatographic analysis, 82% yield).

Comparative Example A

Liquid Phase Preparation of 3-isocyanatopropyltriethoxysilane

Ethyl N-(3-triethoxysilylpropyl)carbamate (348.7 g, 1.19 mols) was heated at 200° C. for 5 hours at 50 mm Hg pressure. The glass flask reactor was fitted with a 10 tray Oldershaw distillation column to remove the isocyanatoalkylsilane product to a receiver as it was formed. Product cuts were collected at 149°–156° C./50 mm Hg totalling 218.5 g, containing 210 g of 3-isocyanatopropyltriethoxysilane (71% yield), plus a mid-cut at 154°–168° C./50 mm Hg (38.9 g) which contained only 51.6% of 3-isocyanatopropyltriethoxysilane, with 11.1% of cyclic silyl carbamate, 18.5% of starting carbamate, and 17.5% of uneluted heavies by gas chromatographic analysis. If analysis. If the 3-isocyanatopropyltriethoxysilane in this crude mid-cut is added to that in the purer cuts, the total yield is 78.3%, which compares well with the 72.9% yield calculated from Example 2, U.S. Pat. No. 3,607,901, also a liquid phase example. This example, and that of U.S. Pat. No. 3,607,901, of liquid phase preparation of isocyanatoorganosilanes, show that yields are lower and contents of close-boiling cyclic silyl carbamate contaminants are higher than those of the present invention, which is a gas phase process.

Comparative Example B

Liquid Phase Stability of 3-isocyanatopropyltriethoxysilane

A sample of 3-isocyanatopropyltriethoxysilane, as prepared in Comparative Example A, was heated under an inert atmosphere at 140° C. After 6 hours, the purity had dropped to 85.6%, with 12.1% of cyclic silyl carbamate being present. After 2 days at 140° C., the sample contained 57.8% of heavies, as determined by gas chromatographic analysis. This example, in conjunction with Example 4 of the present invention, shows that isocyanatoorganosilanes are much less stable under liquid phase conditions than they are under gas phase conditions even though temperatures are much higher under gas phase conditions.

The principles, preferred embodiments, and modes of operation of the present invention have been described in the foregoing specification. The invention which is intended to be protected herein, however, is not to be construed as limited to the particular forms disclosed, since they are regarded as illustrative rather than restrictive. Variations and changes may be made by those skilled in the art without departing form the spirit of the invention.

What is claimed is:

1. A method for preparing an isocyanatoorganosilane comprising vaporizing a carbamatoorganosilane and heating said vaporized carbamatoorganosilane in a reaction zone at an elevated temperature for a time sufficient to form said isocyanatoorganosilane.

2. The method of claim 1 wherein the isocyanatoorganosilane has the formula $R_x(R''O)_{3-x}SiR'NCO$, wherein x is an integer having a value of 0, 1, 2, or 3, each R separately represents an alkyl group of 1 to 12 carbon atoms, a halogenated alkyl group of 1 to 12 carbon atoms, a cycloalkyl group or a halogenated cycloalkyl group of 5 to 8 carbon atoms, an aryl group of 6 to 14 carbon atoms, or an alkaryl or aralkyl group of 7 to 15 carbon atoms, each R'' separately represents R, a silyl group $R_3Si-$, a siloxy group $R_3Si(OSiR_2)_m-$ wherein m is an integer having a value of 1 to 4, or two R'' groups together may form a divalent siloxy group of the formula $-SiR_2(OSiR_2)_n-$ wherein n is an integer having a value of 3, 4, or 5, and R is as defined above, and R' is a divalent hydrocarbon group of 1 to 20 carbon atoms attached to silicon by a silicon-carbon bond, and wherein R and R' optionally contain heteroatom functional groups selected from the group consisting of ether, thioether, sulfone, ketone, ester, amide, nitrile, or halogen.

3. The method of claim 1 wherein the elevated temperature is between 300° C. and 600° C. and said reaction zone is maintained at a reduced pressure between 10 mm and 760 mm Hg.

4. The method of claim 2 wherein R' is selected from the group consisting of divalent alkylene groups, divalent arylene groups, divalent alkarylene groups, and divalent arylene groups.

5. The method of claim 2 wherein R is a methyl group or an ethyl group and the R goups attached to oxygen atoms are the same, x is 0 or 1, and R' is $-(C_nH_{2n})-$, where n is an integer of 3 to 6.

6. The method of claim 1 wherein the carbamatoorganosilane is selected from the group consisting of $(MeO)_3Si(CH_2)_3NHCO_2Me$, $Me(MeO)_2Si(CH_2)_3NHCO_2Me$, and $(EtO)_3Si(CH_2)_3NHCO_2Et$ where Me is a methyl group and Et is an ethyl group.

7. The method of claim 2 wherein the isocyanatoorganosilane is selected from the group consisting of $Me(Me_3SiO)_2Si(CH_2)_3NCO$, $(Me_3SiO)_3Si(CH_2)_3NCO$, $(OSiMe_2)_3OSiMe(CH_2)_3NCO$, and $(OSiMe_2)_4OSiMe(CH_2)_3NCO$, where Me is a methyl group.

8. The method of claim 1 wherein the reaction zone comprises a continuous flow-through metal tube reactor with means for vaporizing said carbamatoorganosilane and for collecting said isocyanatoorganosilane.

9. An isocyanatoorganosilane having the formula $R_x(R''O)_{3-x}SiR'NCO$, wherein x is an integer having a value of 0, 1, 2, or 3, each R separately represents an alkyl group of 1 to 12 carbon atoms, a halogenated alkyl group of 1 to 12 carbon atoms, a cycloalkyl group or a halogenated cycloalkyl group of 5 to 8 carbon atoms, an aryl group of 6 to 14 carbon atoms, or an alkaryl or aralkyl group of 7 to 15 carbon atoms, each R'' separately represents R, a silyl group $R_3Si-$, a siloxy group $R_3Si(OSiR_2)_m-$ wherein m is an integer having a value of 1 to 4, or two R'' groups together may form a divalent siloxy group of the formula $-SiR_2(OSiR_2)_n-$ wherein n is an integer having a value of 3, 4, or 5, and R is as defined above, and R' is selected from the group consisting of $-CH_2CH_2CMe_2-$, $-CH_2CH_2CHMeCH_2-$, $-CH_2CH_2CMe_2CH_2-$, and $-CH_2CHMeCH_2-$, where Me is a methyl group.

* * * * *

UNITED STATES PATENT AND TRADEMARK OFFICE
CERTIFICATE OF CORRECTION

PATENT NO. : 5,393,910
DATED : February 28, 1995
INVENTOR(S) : Mark Paul Bowman and Jeffrey Y.P. Mui It is certified that error appears in the above-identified patent and that said Letters Patent is hereby corrected as shown below:

Col.10, line 8, please delete the word "goup" and insert therefor --group--.

Signed and Sealed this

Fourth Day of July, 1995

*Attest:*

BRUCE LEHMAN

*Attesting Officer*  *Commissioner of Patents and Trademarks*